United States Patent [19]

Hesse

[11] Patent Number: Plant 5,721

[45] Date of Patent: Apr. 15, 1986

[54] CHRYSANTHEMUM PLANT NAMED STOPLIGHT

[75] Inventor: Peter S. Hesse, Bradenton, Fla.

[73] Assignee: Pan American Plant Company, Parrish, Fla.

[21] Appl. No.: 660,404

[22] Filed: Oct. 12, 1984

Related U.S. Application Data

[63] Continuation of Ser. No. 484,442, Apr. 13, 1983, abandoned.

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of chrysanthemum named Stoplight having single capitulum type, flat capitulum form, brilliant red ray florets, diameter of 65–80 mm. across face of capitulum, and by its resistance to fading under high light and high temperature.

2 Drawing Figures

This is a continuation of application Ser. No. 484,442, filed Apr. 13, 1983, now abandoned.

The present invention comprises a new and distinct cultivar of *Chrysanthemum morifolium,* Ramat., hereinafter referred to by the cultivar name Stoplight.

Stoplight is a product of a planned breeding program which had the objective of creating new chrysanthemum cultivars with single capitulum type, brilliant red ray floret color, 9 week response, and the ability to produce commercially acceptable quality in year round pot mum programs. Such traits in combination were not present in previously available commercial cultivars.

Stoplight was originated from a self pollination of the cultivar designated P7-400 made in a controlled breeding program in West Chicago, Ill. in 1979. Stoplight was discovered and selected as one flowering plant within the progeny of the stated parentage by Peter S. Hesse in September, 1980 in a controlled environment in West Chicago, Ill.

The first act of asexual reproduction of Stoplight was accomplished when vegetative cuttings were taken from the initial selection on Nov. 15, 1980 in a controlled environment in West Chicago, Ill. by a technician working under formulations established and supervised by Peter S. Hesse. Horticultural examination of selected units initiated Feb. 26, 1981 has demonstrated that the combination of characteristics as herein disclosed for Stoplight are firmly fixed and are retained through successive generations of asexual reproduction.

Stoplight has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Stoplight, which in combination distinguish this chrysanthemum as a new and distinct cultivar:

1. Flat capitulum form.
2. Single capitulum type.
3. Brilliant red ray florets.
4. Diameter across the face of the capitulum 65–80 mm.

5. Yellow-green (immature) to yellow (mature) disc florets.
6. Does not fade significantly under high light and high temperatures.
7. Medium pot plant height of about 300 mm. from edge of the pot.
8. Semi-upright branching pattern.

Of the many commercial cultivars known to the present inventor, the most similar in comparison to Stoplight is Spark, disclosed in U.S. Plant Pat. No. 3,946, granted Aug. 24, 1976. In comparison to Spark, Stoplight has larger flowers, a brighter red color, the petals are more upright (cupped capitulum), and it is more resistant to fading under high light and temperature conditions. The disc floret color, capitulum form and capitulum type are similar to those same characteristics of Spark.

The accompanying photographic drawings show typical inflorescence and foliage characteristics of Stoplight, with colors being as nearly true as possible with illustrations of this type. Sheet 1 is a color photograph of Stoplight. Sheet 2 is a black and white print of a photo showing typical leaves (abaxial view) at various stages of development.

It should be noted that the illustrated flower color in Sheet 1 is a brighter red than the actual flower color, specified below. The true flower color is essentially identical to the flower color illustrated in U.S. Plant Pat. No. 4,328, granted Oct. 31, 1978.

In the following description color references are made to The Royal Horticultural Society Colour Chart. The color values were determined between 8:00–9:00 A.M. on Nov. 17, 1982 under 2000–3000 foot candle intensity at Parrish, Fla.

Classification:

*Botanical.*—*Chrysanthemum morifolium,* Ramat. cv Spotlight.

*Commercial.*—Daisy Pot Mum.

I. Inflorescence:

A. *Capitulum.*—Form: Flat. Type: Daisy. Diameter Across Face: 65–80 mm.

B. *Corolla of ray florets.*—Color (general tonality from a distance of three meters): Red. Color (upper surface): 181A. Color (lower surface): 46A.

C. *Corolla of disc florets.*—Color (mature): Yellow. Color (immature): Yellow-green.

D. *Reproductive organs.*—Androecium: Present only in disc florets; numerous. Gynoecium: Present in both ray and disc florets; numerous.

II Plant

A. *General appearance.*—Height: Upright approximately 300 mm.

B. *Foliage.*—Color (abaxial): 147B. Color (adaxial): 147A. Shape: Deeply lobed and slightly serrated.

I claim:

1. A new and distinct cultivar of chrysanthemum named Stoplight, as described and illustrated, and particularly characterized by its single capitulum type, flat capitulum form, brilliant red ray florets, diameter of 65–80 mm. across face of capitulum, and by its resistance to fading under high light and high temperatures.

* * * * *

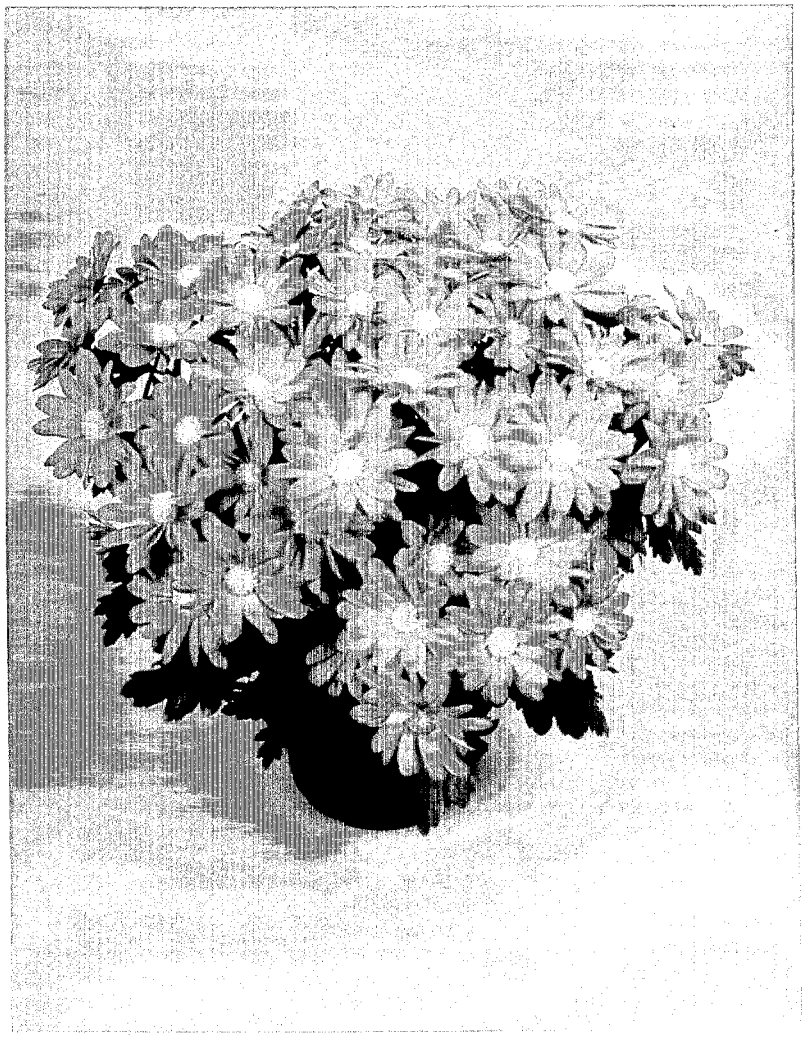

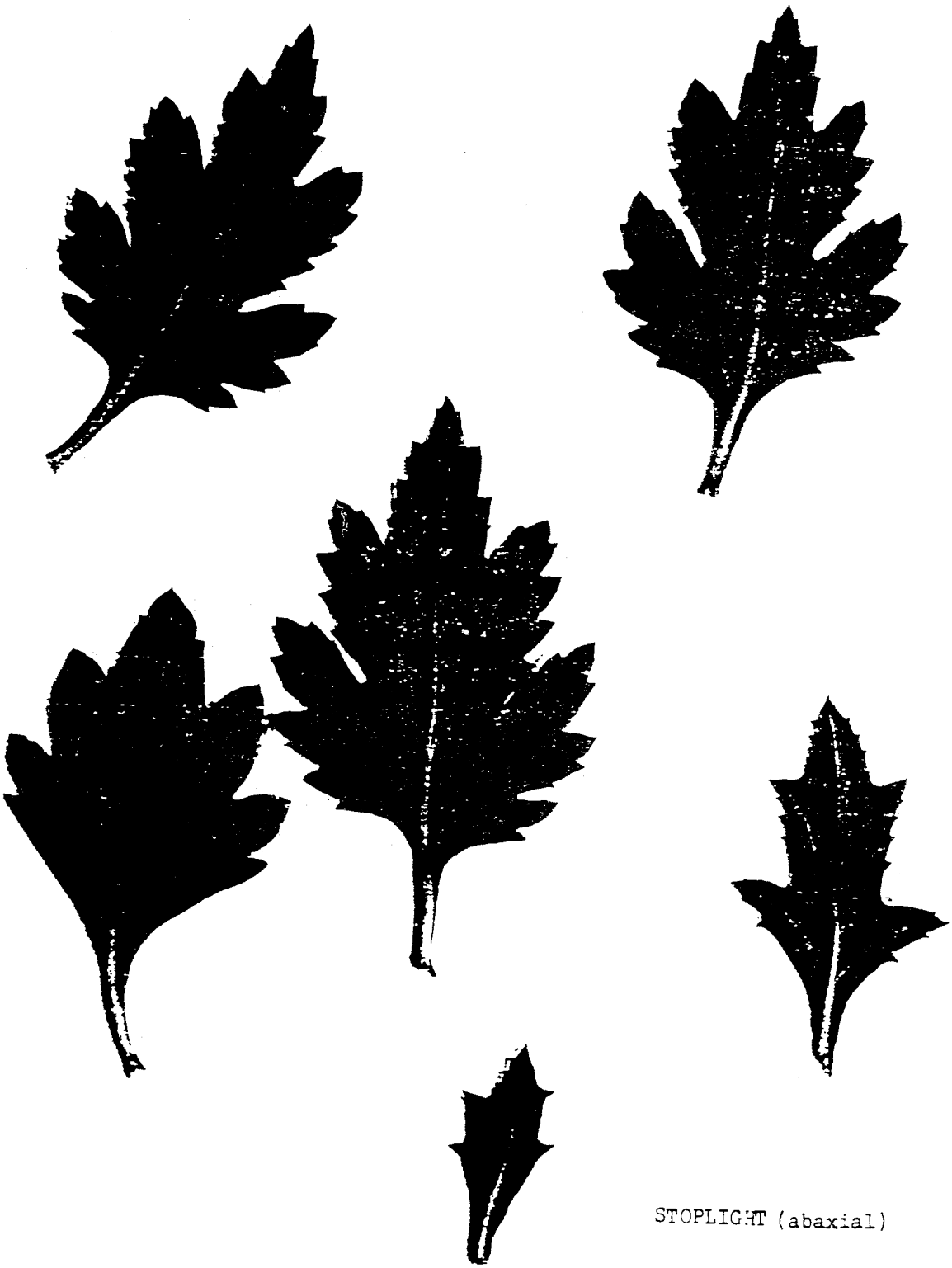
STOPLIGHT (abaxial)